United States Patent [19]

Chern et al.

[11] Patent Number: 5,340,814

[45] Date of Patent: * Aug. 23, 1994

[54] 3-SUBSTITUTED METHYL-2,3-DIHYDROIMIDAZO[1,2-C] QUINAZOLINE DERIVATIVES, THE PREPARATION AND USE THEREOF

[75] Inventors: Ji-Wang Chern; Guan-Yu Lu; Yue-Jun Lai; Mao-Hsiung Yen; Pao-Luh Tao, all of Taipei, Taiwan

[73] Assignee: National Science Council, Taipei, Taiwan

[ * ] Notice: The portion of the term of this patent subsequent to Oct. 27, 2009 has been disclaimed.

[21] Appl. No.: 961,095

[22] Filed: Oct. 14, 1992

Related U.S. Application Data

[63] Continuation-in-part of Ser. No. 744,534, Aug. 13, 1991, Pat. No. 5,158,953.

[51] Int. Cl.$^5$ .................. A61K 31/505; C07D 487/04
[52] U.S. Cl. ..................... 514/267; 544/250; 544/285; 544/286
[58] Field of Search ........................ 544/250; 514/267

[56] References Cited

U.S. PATENT DOCUMENTS 5,120,736  6/1992  Houziaux et al. ............... 544/369
5,128,338  7/1992  Bourguignon et al. .......... 544/250
5,158,953  10/1992  Chern et al. ..................... 544/250

OTHER PUBLICATIONS

*Medicinal Chemistry* (2nd Ed.) by Alfred Burger (Interscience Publishers), pp. 72–78 (1960).
Ji-Wang Chern, "Studies on Quinazolinones, 3:1 Novel and Efficient . . . ", *Bioorganic & Medicinal Chemistry Letters*, vol. 1, No. 11, pp. 571–574, 1991.
N. Seki, et al., "Electrical and Mechanical Properties . . . ", *Br. J. Pharmacol.* (1988), 93, 702–714.
Yamanouchi et al., An article from Drug of the Future (1989), p. 400.

*Primary Examiner*—Emily Bernhardt
*Attorney, Agent, or Firm*—Konneker Bush Hitt & Chwang

[57] ABSTRACT

The present invention provides a novel series of 3-substituted methyl-2,3-dihydroimidazo[1,2-c]quinazoline compounds. These compounds are found useful as an active ingredient for the treatment of hypertension and dysuria.

8 Claims, No Drawings

3-SUBSTITUTED METHYL-2,3-DIHYDROIMIDAZO[1,2-C] QUINAZOLINE DERIVATIVES, THE PREPARATION AND USE THEREOF

This application is a continuation-in-part of U.S. patent application Ser. No. 07/744,534, filed on Aug. 13, 1991, now U.S. Pat. No. 5,158,953, issued Oct. 27, 1992.

FIELD OF THE INVENTION

The present invention relates to new 3-substituted methyl-2,3-dihydroimidazo[1,2-c]quinazoline derivatives I–IV and their pharmaceutically acceptable salts, the preparation thereof by methods per se and the use of the new compounds in therapy, particularly for the treatment or prevention of high blood pressure and dysuria.

BACKGROUND OF THE INVENTION

A class of antihypertensive agents such as prazosin, disclosed in U.S. Pat. No. 3,511,836, which is a 2-substituted quinazoline derivative containing a quinazoline ring system, has been proven effective in the clinic acting as a $\alpha_1$-adrenoceptor antagonist. While 3-substituted quinazolinones such as ketanserin, thioketanserin disclosed in U.S. Pat. No. 4,335,127, and SGB-1534 disclosed in *Japan J. Pharmacol.* 1987, 44, 35 have been found to have antihypertensive activities by a serotonin-$S_2$ and $\alpha_1$-adrenoceptor antagonist, respectively. During the course of our synthetic studies on the fused quinazoline ring system, we have synthesized the angularly tricyclic condensed quinazoline derivatives such as 2-substituted methyl-2,3-dihydroimidazo[1,2-c]quinazoline derivatives which would possess a rigid structural feature necessary to elicit the biological activities of both ketanserin and SGB-1534 and have been shown potent lowering blood pressure acting as a $\alpha_1$-adrenoceptor antagonist (U.S. patent application Ser. No. 07/744,534, filed by Ji-Wang Chern, et al. and is now U.S. Pat. No. 5,158,953. Recently, it was reported in *Drug of the Future*, 1989, 14, 400 and *Brit. J. Pharmacol.* 1988, 93, 702–14 that $\alpha_1$-adrenoceptor antagonists can be used for the treatment of dysuria which is due to the prostatauxe.

Nevertheless, more potent and clinically effective antihypertensive agents are still needed.

DETAILED DESCRIPTION OF THE INVENTION

Accordingly, one general object of the present invention is to develop a more potent and clinically effective antihypertensive and anti-dysuria agents.

Another object of this invention is to provide new and useful 3-substituted methyl-2,3-dihydroimidazo[1,2-c]quinazoline derivatives I–IV and pharmaceutically acceptable salts thereof.

Another object of this invention is to provide a process for production of the 3-substituted methyl-2,3-dihydroimidazo[1,2-c]quinazoline derivatives I–IV and salts thereof.

A further object of this invention is to provide a pharmaceutical composition containing, as an active ingredient, said 3-substituted methyl-2,3-dihydroimidazo[1,2-c]quinazoline derivatives I–IV and salts thereof.

Still further object of this invention is to provide a use of 3-substituted methyl-2,3-dihydroimidazo[1,2-c]quinazoline derivatives I–IV and pharmaceutically acceptable salts thereof for manufacture of medicaments for the therapeutic treatment of high blood pressure and dysuria.

A series of novel compounds represented by formulas I–IV shown below, and salts thereof have been developed and they exhibit excellent antihypertensive activities.

The new 3-substituted methyl-2,3-dihydroimidazo[1,2-c]quinazoline derivatives of this invention can be represented by the following general formulas I–IV including their racemic mixtures of optically active compounds and optically pure R and S stereoisomers:

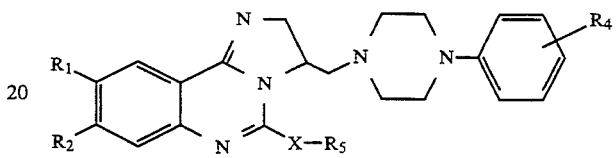

wherein:

X is S or O, when X is S, the formula represents I; and when X is O, the formula represents II:

$R_1$ is halogen, hydrogen, $C_1$–$C_6$ alkyl, trifluoromethyl, or $C_1$–$C_6$ alkoxy;

$R_2$ is halogen, hydrogen, $C_1$–$C_6$ alkyl, trifluoromethyl, or $C_1$–$C_6$ alkoxy;

$R_4$ is halogen, hydrogen, methoxy, trifluoromethyl, $C_1$–$C_4$ alkyl, nitro, acetyl, cyano or hydroxy group;

$R_5$ is $C_1$–$C_4$ alkyl or aryl-($C_1$–$C_4$)alkyl group;

or pharmaceutically acceptable salts thereof;

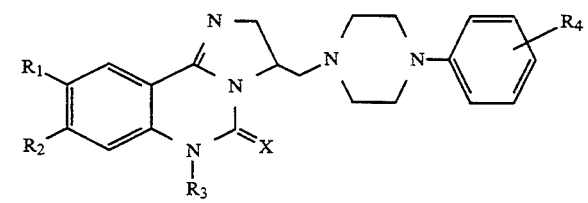

wherein:

$R_3$ is hydrogen, $C_1$–$C_4$ alkyl or aryl-($C_1$–$C_4$)alkyl group, when $R_3$ is hydrogen, the formula represents III; and when $R_3$ is $C_1$–$C_4$ alkyl or aryl-($C_1$–$C_4$)alkyl group, the formula represents IV;

X is O or S;

$R_1$ is halogen, hydrogen, $C_1$–$C_6$ alkyl, trifluoromethyl, or $C_1$–$C_6$ alkoxy;

$R_2$ is halogen, hydrogen, $C_1$–$C_6$ alkyl, trifluoromethyl, or $C_1$–$C_6$ alkoxy;

$R_4$ is halogen, hydrogen, methoxy, trifluoromethyl, $C_1$–$C_4$ alkyl, nitro, acetyl, cyano or hydroxy group;

or pharmaceutically acceptable salts thereof.

Examples of the pharmaceutically acceptable salt include salts with inorganic acids, such as hydrochloride, hydrobromide, sulfate, and phosphate; those with organic acids, such as acetate, maleate, tartrate, methanesulfonate, benzenesulfonate, and toluenesulfonate; and those with amino acids, such as arginine, aspartic acid and glutamic acid.

Although the compound of the present invention may also be present as a hydrates or as a stereoisomer, it is to be understood that these hydrates and stereoisomers are also included in the scope of the present invention.

The term "halogen" here refers to fluorine, chloride and bromine. Fluorine and particularly chlorine are preferred.

Broadly, a process for preparing the new compounds I–IV of the present invention comprises the following steps:

a) reacting a compound, of formula V

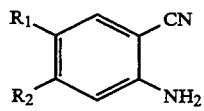

wherein $R_1$ and $R_2$ represent the same groups as defined above, with carbon disulfide in pyridine to give a compound of formula VI,

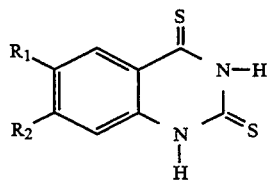

wherein $R_1$ and $R_2$ represent the same groups as defined above;

b) reacting the resulting compound VI with an alkylating agent having a formula of $R_5$—Y to yield a compound of formula VII,
wherein $R_5$ represents the same groups as defined above, and Y represents halogen;

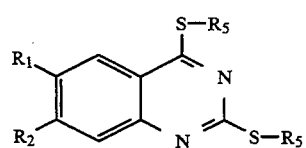

wherein $R_1$, $R_2$ and $R_5$ represent the same groups as defined above;

c) reacting the resulting compound VII with allylamine to yield a compound of formula VIII,

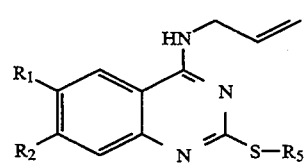

wherein $R_1$, $R_2$ and $R_5$ represent the same groups as defined above;

d) halocyclizating the resulting compound VIII to yield a compound of formula IX,

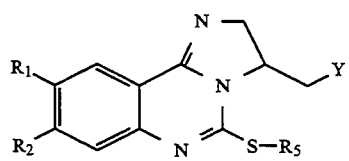

wherein $R_1$, $R_2$, $R_5$ and Y represent the same groups as defined above;

e) reacting the resulting compound IX with a suitable side chain such as a compound of formula X to obtain the compound I,

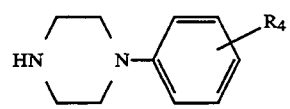

wherein $R_4$ represents the same groups as defined above;

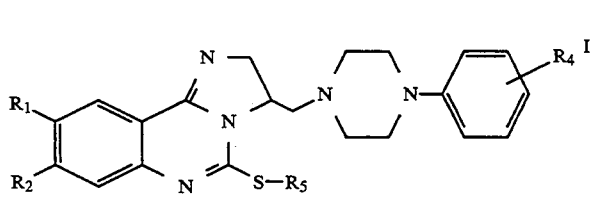

wherein $R_1$, $R_2$, $R_4$ and $R_5$ represent the same groups as defined above; and f) treating the compound I with a compound having a formula of $R_5$—OH in the presence of a base under appropriate conditions to afford the compound II; or g) treating the compound I with a compound having a formula of $R_5$—OH in the presence of a base under appropriate conditions to afford the compound III, wherein $R_5$ represents the same groups as defined above;

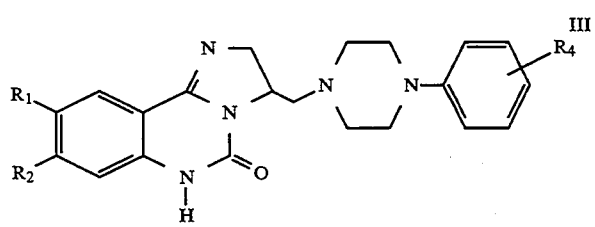

wherein $R_1$, $R_2$, and $R_4$ represent the same groups as defined above; and further h) reacting the compound III with an alkylating agent of formula $R_3$—Y to obtain the compound IV, wherein R3 is $C_1$–$C_4$ alkyl or aryl-($C_1$–$C_4$)alkyl group.

The reaction in step a) can be carried out in any suitable solvent as long as it does not interfere with the reactants can be used. The reaction is performed usually at refluxed temperature and completed in two hours.

The alkylation of compound VI in step b) is carried out in the presence of a base, such as aqueous sodium hydroxide. The reaction is usually completed at room temperature in about three hours.

The reaction in step c) can be carried out in either the absence or presence of a suitable solvent. Any solvent which does not influence the reaction can be used, such as water, alcohols, ethers and dimethylsulfoxide. The reaction usually is carried out in a stainless bomb at 130° C. and completed in about 24 hours.

The halocyclization of the compound VIII in step d) can be carried out in the presence of N-halosuccimide or halogen and with or without a suitable solvent. Any solvent which does not influence the reaction can be used, such as water, alcohols, ethers and dimethylsulfoxide. The reaction usually is carried out at room temperature and completed in about 12 hours.

The reaction between IX and the appropriate side chain X in step e) can be carried out in the presence of a suitable base, such as trimethylamine, sodium bicarbonate and sodium carbonate, in a suitable solvent, such as acetonitrile, dioxane, dimethylformamide (DMF) and dimethylacetamide (DMAC), at a temperature of 50°–120° C., and for a period of 2–24 hours.

The prefer reaction temperature of the reaction in step f) is in a range from 0° C. to 55° C. Examples of the base which can be used include inorganic bases such as sodium hydroxide, sodium carbonate, potassium carbonate, sodium hydrocarbonate, potassium hydrocarbonate, silver carbonate, cesium carbonate and the like; and organic bases such as triethyl amine, pyridine, N,N-dimethylaniline, N-methylmorpholine, DBU, DBN and the like. In the above reaction, an excess amount of side chain $R_5$—OH can be used as a base.

The prefer temperature of the reaction in step g) is about 70° C. Examples of the base which can be used include inorganic bases such as sodium hydroxide, sodium carbonate, potassium carbonate, sodium hydrocarbonate, potassium hydrocarbonate, silver carbonate, cesiumcarbonate. In the above reaction, an excess amount of side chain $R_5$—OH can be used as a base.

The alkylation of the compound III in step h) is carried out in the presence of a base such as aqueous sodium hydroxide. The reaction is usually completed at room temperature in about three hours.

The compounds of formula I-IV and their pharmaceutically acceptable salts of the present invention showed excellent antihypertensive activity and are, therefore, useful as pharmaceuticals.

The pharmacological activities of the compounds of the present invention are described in the following experiment. In this experiment, the test compounds used are as follows.

ANTIHYPERTENSIVE ACTIVITY

Adult cats of either sex, 2–3 Kg, anesthetized with pentobarbital sodium (30 mg/Kg i.p.) were used. The trachea was intubated to provide artificial respiration with air by means of a Harvard respirator (respiration rate=6–20/min and colume=40–50 ml/stroke). Both femoral artery and vein were cannulated with PE 150 to monitor blood pressure and for drug administration respectively. Body temperature was maintained at 37.5° C. with a heating pad and monitored with a rectal thermometer. Blood pressure was measured with a Statham P23D pressure transducer via a polyethylene cannula conducted to a right femoral artery. Heart rate was measured through a Grass Model 7B tachograph preamplifier triggered by the pulses of arterial blood pressure. All data were recorded on a Grass Model 7B polygraph. The results are given in Table 1.

TABLE 1

| Compounds | dose | MBP (2 hr) |
|---|---|---|
| Example 6 | 1 mg/Kg | 70 mmHg |
| Example 9 | 1 mg/Kg | 30 mmHg |
| Example 16 | 1 mg/Kg | 23 mmHg |
| Example 18 | 1 mg/Kg | 50 mmHg |
| Example 21 | 1 mg/Kg | 35 mmHg |
| Example 22 | 1 mg/Kg | 50 mmHg |
| Example 23 | 1 mg/Kg | 63 mmHg |
|  | 0.25 mg/Kg | 40 mmHg |

METHODS OF BINDING STUDIES

1. Preparation of Membranes for Binding Studies

Rat brain cortex membranes were prepared for [$^3$H] prazosin or [$^3$H] clonidine binding by homogenizing tissues in 0.32M sucrose buffered with 50 mM Tris buffer (pH 7.4) in a tissue/buffer ratio of 1:10. After the removal of nuclei by centrifugation at 1000×g for 10 min, $P_2$ membranes were pelleted by centrifuging the supernatant at 22,000×g for 20 min. After two periods of centrifugation at 22,000×g and resuspension in fresh buffer, the membrane suspension (about 2 mg/ml protein) was ready for use.

2. Binding Assays $\alpha_1$-Adrenergic receptor binding assays (in triplicate) were carried out with 0.2 nM [$^3$H] prazocin in a final volume of 1.0 ml of Tris buffer at pH 7.4 for 30 min at room temperature, using 10 $\mu$M phentolamine to determine non-specific binding. The concentrations of synthetic compounds for competition binding were in the range of 0.1–200 nM. $\alpha_2$-adrenergic receptor binding assays (in triplicate) were carried out with 1 nM [$^3$H] clonidine in the presence of 10 mM $MgCl_2$ and in a final volume of 1.0 ml of Tris buffer at pH 7.4 for 30 min at room temperature, using 10 $\mu$M clonidine to determine non-specific binding. The concentrations of synthetic compounds for competition binding were in the range of 0.1–100 $\mu$M. After binding had reached equilibrium, incubations were terminated by collecting the membranes on whatman GF/B filters; the filters were washed twice with 5 ml of 50 mM Tris buffer (pH 7.4) at 4° C. The amount of membrane protein used in each assay was in the range of 300–400 $\mu$g, as determined by the method of Lowry et al. The results are given in Table 2.

Materials

[$^3$H]prazocin (76.6 Ci/mmol) and [$^3$H]clonidine (47.0 Ci/mmol) were purchased from NEN. All other chemicals used were reagent grade and were purchased from Sigma (St. Louis, Mo.).

TABLE 2

$\alpha_1$ and $\alpha_2$-Adrenergic Receptor Binding Affinities for Imidazo[1,2-c]quinazoline Derivatives

| Compounds | $\alpha_1$ Binding (Ki, nM) | $\alpha_2$ Binding (Ki, nM) | $\alpha_2/\alpha_1$ ratio |
|---|---|---|---|
| Example 5 | >10 | | |
| Example 6 | 0.54 ± 0.09 | | |
| Example 7 | 48.9 ± 20.4 | 8356 ± 588 | 171 |
| Example 9 | 0.34 ± 0.06 | 180.4 ± 7 | 529 |
| Example 12 | 0.07 ± 0.007 | | |
| Example 14 | >100 | | |
| Example 16 | 0.11 ± .0.02 | | |
| Example 17 | 1.75 ± 0.5 | 962 ± 29 | 566 |
| Example 18 | 0.45 ± 0.09 | | |
| Example 19 | 5.76 ± 0.48 | | |
| Example 21 | 0.58 ± 0.07 | | |
| Example 22 | 0.068 ± .0.006 | | |
| Example 23 | 0.36 ± 0.05 | | |
| SGB-1534 | 0.25 ± 0.06 | | |

Preferred compounds are those prepared by the following Examples:

EXAMPLE 5

3-[4-(1-Phenyl)piperazinyl]methyl-5-methylthio-2,3-dihydroimidazo[1,2-c]quinazoline

EXAMPLE 6

3-{4-[1-(2-methoxyphenyl)piperazinyl]}methyl-5-methylthio-2,3-dihydroimidazo[1,2-c]quinazoline

EXAMPLE 9

3-{4-[1-(2-chlorophenyl)piperazinyl]}methyl-5-methylthio-2,3-dihydroimidazo[1,2-c]quinazoline

EXAMPLE 12

3-{4-[1-(2-Methoxyphenyl)piperazinyl]}methyl-5-methoxy-2,3-dihydroimidazo[1,2-c]quinazoline

EXAMPLE 13

3-{4-[1-(phenyl)piperazinyl]}methyl-5-methoxy-2,3-dihydroimidazo[1,2-c]quinazoline

EXAMPLE 14

3-{4-[1-(2-chlorophenyl)piperazinyl]}methyl-5-methoxy-2,3-dihydroimidazo[1,2-c]quinazoline

EXAMPLE 17

3-(4-Phenyl-1-piperazinyl)-methyl-2,3-dihydroimidazo[1,2-c]quinazolin-5(6H)-one

EXAMPLE 18

3-{4-[1-(2-methoxyphenyl)piperazinyl]}methyl-2,3-dihydroimidazo[1,2-c]quinazolin-5(6H)-one

EXAMPLE 21

3-{4-[1-(2-chlorophenyl)piperazinyl]}methyl-2,3-dihydroimidazo[1,2-c]quinazolin-5(6H)-one

EXAMPLE 22

3-{4-[1-(2-chlorophenyl)piperazinyl]}methyl-6-methyl-2,3-dihydroimidazo[1,2-c]quinazolin-5(6H)-one

EXAMPLE 23

3-{4-[1-(2-methoxyphenyl)piperazinyl]}methyl-6-methyl-2,3-dihydroimidazo[1,2-c]quinazolin-5(6H)-one

EXAMPLE 29

3-[4-(1-phenyl)piperazinyl]methyl-5-methylthio-8,9-dimethoxy-2,3-dihydroimidazo[1,2-c]quinazoline Compounds of the invention may be formulated for use in a pharmaceutical composition. Accordingly, in a further aspect of the invention, there is provided a pharmaceutical composition which comprises a compound of formula I-IV or pharmaceutically acceptable salt thereof together with a pharmaceutically acceptable carrier or excipient.

A composition which may be administered by the oral route to humans may be compounded in the form of a syrup, tablet or capsule. When the composition is in the form of a tablet, any pharmaceutical carrier suitable for formulating such as solid compositions may be used, for example magnesium sterate, starch, lactose, glucose and flavor. The compounds may also be presented with a sterile liquid carrier for injection.

The present invention is now illustrated in greater detail by the following Examples which are intended to be illustrated and not limiting.

EXAMPLE 1

Quinazolin-2,4(1H, 3H)-dithione

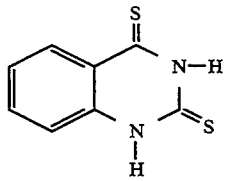

A mixture of anthranilonitrile (3.0 g, 25.4 mmol) and carbon disulfide (10 mL, 0.13 mole) in pyridine (10 mL) was refluxed for 8 hours. After the mixture was cooled to room temperature for 1 hour, ethanol (150 mL) was added to the mixture. The yellowish solid was then collected by filtration and washed with ether (15 mL) to afford 4.53 g (92%) of quinazolin-2,4(1H, 3H)-dithione, mp 234°–237° C. [235°–238° C., reported by E. C. Taylor, et al. in "Heteroxyclic syntheses from o-aminonitriles-XXVII. A. one-step synthesis of fused pyrimidine-dithiones", Tetrahedron, 1967, 23, 891]. $^1$H-NMR (100 MHz, DMSO-$d_6$): $\delta$7.23–7.37 (m, 2H, Ar—H), 7.65–7.81 (m, 1H, Ar—H), 8.23–8.33 (m, 1H, Ar—H), 13.05 (s, 2H, NH$_2$, D$_2$O exchangeable); $^{13}$C-NMR (25 MHz, DMSO-$d_6$): $\delta$116.02, 122.52, 125.04, 129.90, 135.82, 136.11, 170.21, 187.57.

EXAMPLE 2

2,4-Dimethylthioquinazoline

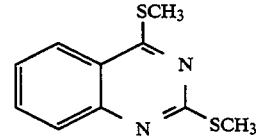

To a solution of quinazolin-2,4(1H, 3H)-dithione (10 g, 51.5 mmol) in 10% aqueous sodium hydroxide solution (50 mL) was added methyl iodide (10 ml, 0.1 mole) dropwise. After the mixture was stirred at room temperature for 24 hours, the white solid was collected by filtration and washed with water (10 mL) to furnish 10.65 g (93%) of 2,4-dimethylthioquinazoline, mp 85° C. $^1$H-NMR (100 MHz, DMSO-$d_6$): $\delta$2.61 (s, 3H, CH$_3$), 2.65 (s, 3H, CH$_3$), 7.53–7.82 (m, 4H, Ar—H).; $^{13}$C-NMR (25 MHz, DMSO-$d_6$): $\delta$12.13, 13.71, 120.23, 123.45, 126.03, 126.56, 134.30, 147.60, 165.78, 170.50.; ms: m/z 221 (M$^+$−1), 206 (M$^+$−15), 188 (M$^+$−60), 159 (M$^+$−62).

EXAMPLE 3

4-Allyl-2'-methylthioquinazoline

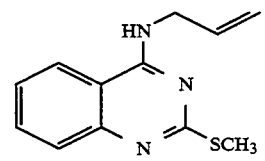

A mixture of 2,4-dimethylthioquinazoline (10 g, 45 mmol) and allylamine (68 mL, 0.9 mol) in acetonitrile (200 mL) was heated in a stainless vessel at 120°–130° C. for 48 hours. The mixture was concentrated in vacuo to 20 mL at 50° C. and was then allowed to set in a refrigerator for 6 hours. The solid was collected by filtration and washed with acetonitrile (10 mL) to give 9.47 g (91%) of 4-allyl-2-methylthioquinazoline. An analytical sample was recrystallized from ethylacetate, mp 133°–135° C.; $^1$H-NMR (100 MHz, DMSO-d$_6$): δ, 2.50 (s, 3H, CH$_3$), 4.16 (t, 2H, J=6.0 Hz, CH$_2$), 5.02–5.26 (m, 2H, CH$_2$), 5.76–6.18 (m, 1H, Ar—H), 7.26–7.74 (m, 3H, Ar—H), 8.18 (d, 1H, J=8.5 Hz, Ar—H), 8.50 (t, 1H, J=5.9 Hz, NH, D$_2$O exchangeable); $^{13}$C-NMR (25 MHz, DMSO-d$_6$): δ13.48, 42.77, 112.67, 115.49, 122.75, 124.10, 125.74, 132.71, 134.65, 149.30, 158.20, 166.37.; ms: m/z 231 (M$^+$), 205 (M$^+$−26), 183 (M$^+$−48). Anal. Calcd for C$_{12}$H$_{13}$N$_3$S (231.31): C, 62.31; H, 18.17; N, 5.66. Found: C, 62.12; H, 17.84; N, 5.70.

EXAMPLE 4

3-Bromomethyl-5-methylthio-2,3-dihydroimidazo[1,2-c]quinazoline

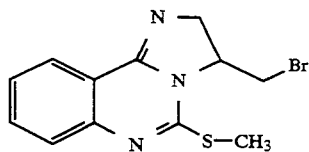

To a suspension of 4-allyl-2-methylthioquinazoline (10 g, 43 mmol) in acetonitrile (50 mL) was added NBS (9 g, 50 mmol) and the mixture turned into a solution. The solution was then stirred at room temperature. After 10 minutes, the white solid gradually prepared and became a suspension again. The reaction was complete within 3 hours. The solid was then collected by filtration and washed with acetonitrile (10 mL) to give 11.75 g (85%) of 3-bromomethyl-5-methylthio-2,3-dihydroimidazo[1,2-c]quinazoline. An analytical sample was recrystallized from acetonitrile, mp 162°–163° C.; $^1$H-NMR (100 MHz, DMSO-d$_6$): δ2.78 (s, 3H, CH$_3$), 4.00–4.43 (m, 4H, 2CH$_2$), 5.45–5.49 (m, 1H, CH), 7.68–7.73 (m, 1H, Ar—H), 7.80 (d, 1H, Ar—H), 8.06 (t, 1H, Ar—H), 8.38 (d, 1H, Ar—H). $^{13}$C-NMR (25 MHz, DMSO-d$_6$): δ13.02, 35.80, 57.37, 59.08, 116.77, 124.98, 125.36, 125.48, 133.06, 145.75, 152.63, 153.69.; ms: m/z 310 (M$^+$), 309 (M$^+$−1), 230 (M$^+$−80), 174 (M$^+$−136) Anal. Calcd for C$_{12}$H$_{12}$N$_3$SBr (310.21): C, 46.46; H, 13.55; N, 3.90. Found: C, 46.60; H, 13.70; N, 3.88.

EXAMPLE 5

3-[4-(1-Phenyl)piperazinyl]methyl-5-methylthio-2,3-dihydroimidazo[1,2-c]quinazoline

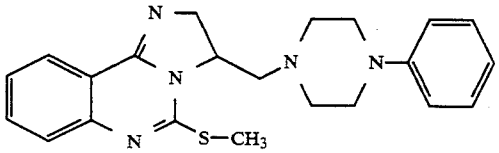

A mixture of 3-bromomethyl-5-methylthio-2,3-dihydroimidazo[1,2-c]quinazoline (3.0 g, 9.7 mmol) and 1-phenylpiperazine (3.0 mL, 18.5 mmol) in acetonitrile (60 mL) was refluxed using an oil bath for 24 hours. The mixture was then concentrated in vacuo to 30 mL at 40° C. The white solid was collected by filtration and washed with water (25 mL) to give 2.13 g (56%) of 3-[4-(1-phenyl)piperazinyl]methyl-5-methylthio-2,3-dihydroimidazo[1,2-c]quinazoline. An analytical sample was recrystallized from acetonitrile, mp 133°–134° C.; $^1$H-NMR (400 MHz, DMSO-d$_6$): δ2.50–2.56 (m, 4H, 2CH$_2$), 2.59 (s, 3H, CH$_3$), 2.68–2.75 (m, 2H, CH$_2$), 3.09–3.13 (m, 4H, 2CH$_2$), 3.92–4.09 (m, 2H, CH$_2$), 4.51 (m, 1H, CH), 6.76 t, J=7.3 Hz, 1H, Ar—H), 6.89 (d, J=7.8 Hz, 2H, Ar—H), 7.17–7.26 (m3H, Ar—H), 7.33 (d, J=7.8 Hz, 1H, Ar—H), 7.56 (t, J=7.8 Hz, 1H, Ar—H), 7.84 (d, J=7.8 Hz, 1H, Ar—, H).; $^{13}$C-NMR (100 MHz, DMSO-d$_6$): δ12.96, 48.02, 52.96, 55.87, 58.68, 59.14, 115.19, 116.79, 118.58, 124.63, 124.94, 125.27, 128.67, 132.64, 145.86, 150.76, 152.26, 153.95.; ms: m/z 391 (M$^+$), 344 (M$^+$−47), 259 (M$^+$−132), 216 (M$^+$−175), 175 (M$^+$−216, 100%), 132 (M$^+$−259). Anal. Calcd for C$_{22}$H$_{25}$N$_5$S (391.51): C, 67.49; H, 17.89; N, 6.43. Found: C, 67.44; H, 17.72; N, 6.48.

EXAMPLE 6

3-{4-[1-(2-methoxyphenyl)piperazinyl]}methyl-5-methylthio-2,3-dihydroimidazo[1,2-c]quinazoline

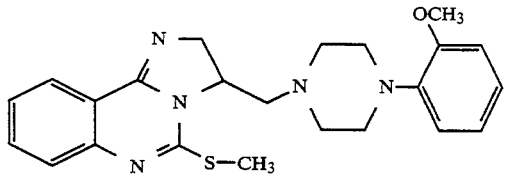

A mixture of 3-bromomethyl-5-methylthio-2,3-dihydroimidazo[1,2-c]quinazoline (3.0 g, 9.7 mmol) and 1-(2-methoxyphenyl)piperazine (3.2 mL, 6.7 mmol) in acetonitrile (60 mL) was refluxed for 24 hours. To the mixture was then added sodium hydrogen carbonate (2.5 g, 30 mmol) and was refluxed for another 12 hours. The mixture was then concentrated in vacuo to 20 mL at 40° C. The white solid was collected by filtration and washed with water (30 mL) to give 3.37 g (82%) of 3-{4-[1-(2-methoxyphenyl)piperazinyl]}methyl-5-methylthio-2,3-dihydroimidazo[1,2-c]quinazoline. An analytical sample was recrystallized from acetonitrile, mp 174°–175° C.; $^1$H-NMR (400 MHz, DMSO-d$_6$): δ2.43–2.56 (m, 4H, 2CH$_2$), 2.59 (s, 3H, —SCH$_3$), 2.86–2.87 (m, 2H, CH$_2$), 2.96 (m, 4H, 2CH$_2$), 3.77 (s, 3H, OCH$_3$), 3.91–4.09 (m, 2H, CH$_2$), 4.52 (m, 1H, CH), 6.87 (s, 2H, Ar—H), 6.92 (s, 2H, Ar—H), 7.25 (t, J=7.3 Hz, 1H, Ar—H), 7.33 (d, J=7.3 Hz, 1H, Ar—H), 7.55 (t, J=6.8 Hz, 1H, Ar—H), 7.83 (d, J=7.3 Hz, 1H, Ar—H).; $^{13}$C-NMR (100 MHz, DMSO-d$_6$): δ12.91, 49.81, 53.33, 55.21, 55.87, 58.67, 59.29, 112.05, 116.75, 117.77, 120.70, 122.11, 124.58, 124.91, 125.23, 132.60, 141.11, 145.83, 151.88, 152.23, 153.96.; ms: m/z 422 (M$^+$), 374 (M$^+$−48), 205 (M$^+$−217, 100%); Anal. Calcd for C$_{22}$H$_{27}$N$_5$SO (421.56): C, 65.53; H, 6.46; N, 16.61. Found: C, 65.21; H, 6.40; N, 16.60.

EXAMPLE 7

3-{4-[1-(3-methoxyphenyl)piperazinyl ]}methyl-5-methylthio-2,3-dihydroimidazo[1,2-c]quinazoline

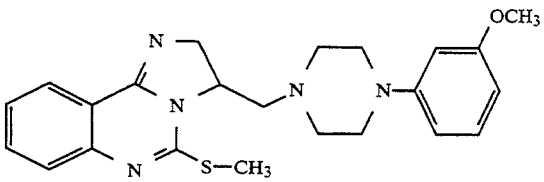

A mixture of 3-bromomethyl-5-methylthio-2,3-dihydroimidazo[1,2-c]quinazoline (3.0 g, 9.7 mmol) and 1-(3-methoxyphenyl)piperazine (3.5 mL, 9.7 mmol) in acetonitrile (60 mL) was refluxed using an oil bath for 12 hours. The mixture was then concentrated in vacuo to 20 mL at 40° C. The solid was collected by filtration and washed with water (30 mL) to give 2.31 g (57%) of 3-{4-[1-(3-methoxyphenyl)piperazinyl]}methyl-5-methylthio-2,3-dihydroimidazo-[1,2-c]quinazoline. An analytical sample was recrystallized from acetonitrile, mp 138°–139° C.; $^1$H-NMR (400 MHz, DMSO-d$_6$): δ2.50–256 (m, 2H, CH$_2$), 2.59 (s, 3H, —SCH$_3$), 2.67–2.74 (m, 4H, 2CH$_2$), 3.11 (m, 4H, 2CH$_2$), 3.70 (s, 3H, OCH$_3$), 3.91–4.05 (m, 2H, CH$_2$), 4.51 (m, 1H, CH), 6.35 (d, J=7.8 Hz, 1H, Ar—H), 6.43 (s, 1H, Ar—H), 6.49 (d, J=8.3 Hz, 1H, Ar—H), 7.09 (t, J=8.3 Hz, 1H, Ar—H), 7.24 (t, J=7.8 Hz, 1H, Ar—H), 7.33 (d, J=8.3 Hz, 1H, Ar—H), 7.54 (t, J=7.8 Hz, 1H, Ar—H), 7.83 (d, J=7.8 Hz, 1H, Ar—H).;$^{13}$C-NMR (100 MHz, DMSO-d$_6$): δ12.96, 47.99, 52.94, 54.68, 55.87, 58,68, 59.12, 101.42, 103.97, 107.88, 116.77, 124.63, 124.94, 125.27, 129.35, 132.64, 145.85, 152.12, 152.25, 153.95, 160.07; ms: m/z 422 (M+), 374 (M+ —48), 259 (M+ —163), 205 (M+ —217, 100%).; Anal. Calcd for C$_{22}$H$_{23}$N$_5$SO (421.56): C, 65.53; H, 6.46; N, 16.61. Found: C, 65.50; H, 6.47; N, 16.66.

EXAMPLE 8

3-{4-[1-(4-methoxyphenyl)piperazinyl]}methyl-5-methylthio-2,3-dihydroimidazo[1,2-c]quinazoline

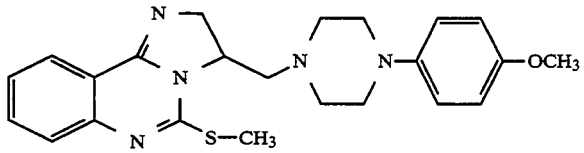

A mixture of 3-bromomethyl-5-methylthio-2,3-dihydroimidazo[1,2-c]quinazoline (3.0 g, 9.7 mmol) and 1-(4-methoxyphenyl)piperazine (3.5 mL, 20.3 mmol) in acetonitrile (60 ml) was refluxed using an oil bath for 24 hours. To the mixture was then added sodium hydrogen carbonate (2.5 g, 30 mmol) and was refluxed for another 12 hours. The mixture was then concentrated in vacuo to 20 mL, at 40° C. The white solid was collected by filtration and washed with water (30 mL) to give 2.27 g (54%) of 3-{4-[1-(2-methoxyphenyl)piperazinyl]}methyl-5-methylthio-2,3-dihydroimidazo[1,2-c]quinazoline. An analytical sample was recrystallized from acetonitrile, mp 133°–135° C.; $^1$H-NMR (400 MHz, DMSO-d$_6$): δ2.51–2.57 (m, 4H, 2CH$_2$), 2.60 (s, 3H, —SCH$_3$), 2.72–2.75 (m, 2H, CH$_2$), 2.99 (m, 4H, 2CH$_2$), 3.68 (s, 3H, OCH$_3$), 3.91–4.03 (m, 2H, CH$_2$), 4.51 (m, 1H, CH), 6.83 (m, 4H, Ar—H), 7.24 (t, J=7.3 Hz, 1H, Ar—H), 7.33 (d, J=7.8 Hz, 1H, Ar—H), 7.54 (t, J=6.8 Hz, 1H, Ar—H),.7.83 (d, J=6.8 Hz, 1H, Ar—H): $^{13}$C-NMR (100 MHz, DMSO-d$_6$): δ12.91, 49.38, 53.07, 55.05, 55.89, 58.65, 59.12, 114.13, 116.77, 117.11, 124.59, 124.89, 125.23, 132.59, 145.19, 145.83, 152.23, 152.78, 153.91. ms: m/z 421 (M+), 406 (M+ —15), 373 (M+ —48), 259 (M+ —162), 216 (M+ —205), 205 (M+ —207, 100%), 162 (M+ —259). Anal. Calcd for C$_{22}$H$_{23}$N$_5$SO (421.56): C, 65.53; H, 6.46; N, 16.60. Found: C, 65.53; H, 6.51; N, 16.61.

EXAMPLE 9

3-{4-[1-(2-chlorophenyl)piperazinyl]}methyl-5-methylthio-2,3-dihydroimidazo[1,2-c]quinazoline

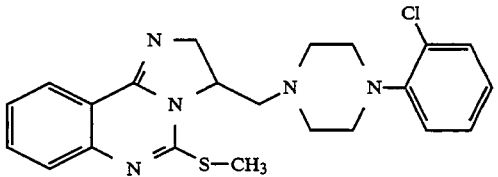

To a suspension of 3-bromomethyl-5-methylthio-2,3-dihydroimidazo[1,2-c]quinazoline (2.0 g, 6.4 mmol) and sodium bicarbonate (0.8 g, 8.8 mmol) in acetonitrile (40 mL) was added 1-(2-chlorophenyl)piperazine hydrochloride (1.9 g, 7.7 mmol). The mixture was refluxed using an oil bath for 24 hours. The white solid was then collected by filtration and washed with water (30 mL) to give 1.23 g (45%) of 3-{4-[1-(2-chlorophenyl)-piperazinyl]}methyl-5-methylthio-2,3-dihydroimidazo[1,2-c]quinazoline. An analytical sample was recrystallized from ethanol, mp 184°–185° C.; $^1$H-NMR (400 MHz, CDCl$_3$): δ2.17–2.54 (m, 2H, CH$_2$), 2.56 (s, 3H, —SCH$_3$), 2.58–2.82 (m, 4H, 2CH$_2$), 2.96–3.02 (m, 4H, 2CH$_2$), 4.05–4.07 (m, 2H, CH$_2$), 4.36–4.37 (m, 1H, CH), 6.86–7.89 (m, 8H, Ar—H); $^{13}$C-NMR (100 MHz, CDCl$_3$): δ13.50, 51.09, 53.81, 56.43, 59.28, 59.68, 117.05, 120.32, 123.64, 125.10, 125.30, 125.74, 127.51, 128.72, 130.57, 132.89, 146.53, 149.17, 153.81, 154.27,; Anal. Calcd for C$_{22}$H$_{24}$N$_5$SCl (425.98): C, 62.03; H, 5.68; N, 16.44. Found: C, 61.72; H, 5.65; N, 16.43.

EXAMPLE 10

3-(3-azaspiro[5,5]undecanyl)methyl-5-methylthio-2,3-dihydroimidazo[1,2-c]quinazoline

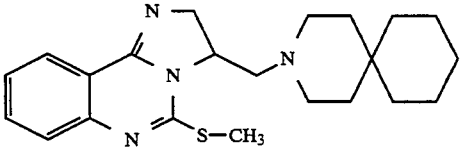

A mixture of 3-bromomethyl-5-methylthio-2,3-dihydroimidazo[1,2-c]quinazoline (3.0 g, 9.7 mmol), 3-azaspiro[5,5]undecane (2.3 mL, 14.2 mmol) and sodium hydrogen carbonate (0.9, 10.7 mmol) in acetonitrile (80 mL) was refluxed using an oil bath for 10 hours. The undissolved solid was filtered and the filtrate was then concentrated in vacuo to 20 mL at 40° C. The white solid was collected by filtration and washed with water (30 mL) to give 2.47 g (67%) of 3-(3-azaspiro[5,5]undecanyl)methyl-5-methylthio-2,3-dihydroimidazo[1,2-c]quinazoline. An analytical sample was recrystallized from acetonitrile, mp 114°–115° C.; $^1$H-NMR (300 MHz, DMSO-d$_6$): δ1.28–1.35 (m, 16H, 8CH$_2$), 2.30 (s, 2H, CH$_2$), 2.37–2.68 (m, 2H, CH$_2$), 2.64 (s, 3H, CH$_3$), 3.83–4.04 (m, 2H, CH$_2$), 4.45 (m, 1H, CH), 7.24 (t, 1H, J=7.4 Hz, Ar—H), 7.32 (d, 1H, J=8.0 Hz, Ar—H), 7.54 (t, 1H, J=7.4 Hz, Ar—H), 7.81 (d, 1H, J=8.0 Hz, Ar—H); ms: m/z 382 (M+), 367 (M+ —15), 336 (M+ —46), 228 (M+ —154). Anal. Calcd for C$_{22}$H$_{30}$N$_4$S (382.56): C, 69.07; H, 7.90; N, 14.64. Found: C, 69.10; H, 7.89; N, 14.65.

EXAMPLE 11

3-(1-imidazolyl)methyl-5-methylthio-2,3-dihydroimidazo[1,2-c]quinazoline

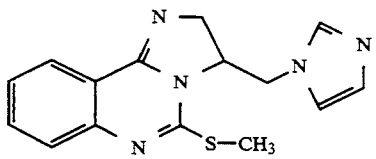

A mixture of 3-bromomethyl-5-methylthio-2,3-dihydroimidazo[1,2-c]quinazoline (3.0 g, 9.7 mmol), imidazole (1.32 g, 19.4 mmol) and sodium hydrogen carbonate (0.8 g, 9.5 mmol) in acetonitrile (80 mL) was refluxed using an oil bath for 96 hours. The undissolved solid was filtered and the filtrate was applied to column chromatography. The desired fraction was collected and was evaporated in vacuo to afford an oily residue. To the residue was added ether 20 mL and set at room temperature for two days. The white solid was collected to give 0.75 g (26%) of 3-(1-imidazolyl)methyl-5-methylthio-2,3-dihydroimidazo[1,2-c]quinazoline. An analytical sample was recrystallized from acetone, mp 97°–99° C.; $^1$H-NMR (100 MHz, DMSO-d$_6$): δ2.64 (s, 3H, CH$_3$), 3.78–4.08 (m, 2H, CH$_2$), 4.25–4.44 (m, 2H, CH$_2$), 4.74 (m, 1H, CH),6.82 (s, 1H, Ar—H), 7.04 (s, 1H, Ar—H), 7.22–7.76 (m, 5H, Ar—H); $^{13}$C-NMR (75 MHz, DMSO-d$_6$): δ, 13.16, 14.43, 57.41, 57.72, 116.70, 119.75, 124.80, 125.29, 125.48, 128.66, 132.97, 137.70, 145.72, 152.48, 153.90; ms: m/z 297 (M+), 250 (M+−47), 228 (M+−69), 216 (M+−81, 100%). Anal. Calcd for C$_{15}$H$_{15}$N$_5$S H$_2$O (315.39): C, 57.12; H, 4.43; N, 22.21. Found: C, 57.10; H, 4.48; N, 22.24.

EXAMPLE 12

3-{4-[1-(2-Methoxyphenyl)piperazinyl]}methyl-5-methoxy-2,3-dihydroimidazo[1,2-c]quinazoline

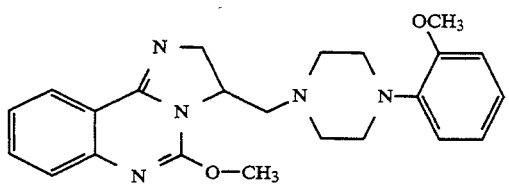

3-{4-[1-( 2-Methoxyphenyl)piperazinyl]}methyl-5-methylthio-2,3-dihydroimidazo[1,2-c]quinazoline (0.57 g, 1.35 mmol) was suspended in 1N ethanolic sodium hydroxide solution (25 mL). It was heated to 55° C. using an oil bath. After 48 hours, the mixture was cooled to room temperature. The solid was then collected by filtration and was washed with water (30 mL) to afford 0.33 g (60%) of 3-{4-[1-(2-methoxyphenyl)-piperazinyl]}methyl-5-methoxy-2,3-dihydroimidazo[1,2-c]quinazoline. An analytical sample was recrystallized from CH$_3$CN, mp 171°–172° C. $^1$H-NMR (400 MHz, DMSO-d$_6$): δ2.47–272 (m, 6H, 3CH$_2$), 2.94 (m, 4H, 2CH$_2$), 3.77 (s, 3H, OCH$_3$), 3.85–4.07 (m, 2H, CH$_2$), 3.96 (s, 3H, OCH$_3$), 4.57–4.59 (m, 1H, CH), 6.86 (s, 2H, Ar—H), 6.91 (s, 2H, Ar—H), 7.19 (t, 1H, J=7.7 Hz, Ar—H), 7.27 (d, 1H, J=8.1 Hz, Ar—H), 7.52 (t, J=7.2 Hz, Ar—H), 7.82 (d, 1H, J=7.7 Hz, Ar—H).; $^{13}$C-NMR (100 MHz, DMSO-d$_6$): δ50.02, 53.47, 54.55, 54.64, 55.28, 58.89, 60.15, 111.89, 116.40, 117.88, 120.81, 122.33, 123.90, 124.94, 125.02, 132.81, 141.16, 147.05, 151.94, 152.17, 153.67.; ms: m/z 404 (M+−1), 355 (M+−150). Anal. Calcd for C$_{23}$H$_{27}$N$_5$O$_2$ (405.50): C, 68.12; H, 6.71; N, 17.27. Found: C, 68.17; H, 6.66; N, 17.30.

EXAMPLE 13

3-{4-[1-(phenyl)piperazinyl]}methyl-5-methoxy-2,3-dihydroimidazo[1,2-c]quinazoline

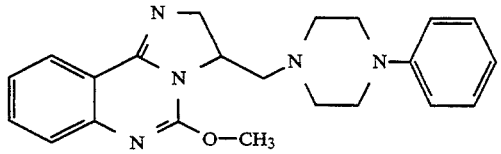

was obtained in 75% yield using a procedure similar to that of Example 12. An analytical sample was recrystallized from acetonitrile, mp 146°–147° C. ms: m/z 375 (M+);. $^1$H-NMR (400 MHz, CDCl$_3$): δ2.51–2.78 (m, 6H, 3CH$_2$), 3.14–3.18 (m, 4H, 2CH$_2$), 4.03 (s, 3H, CH$_3$), 4.06–4.19 (m, 2H, CH$_2$), 4.47–4.53 (m, 1H, CH), 6.85 (t, J=7.3 Hz, 1H, Ar—H), 6.91 (d, J=8.3 Hz, 2H, Ar—H), 7.18 (t, J=7.3 Hz, 1H, Ar—H), 7.26 (t, J=7.8 Hz, 1H, Ar—H), 7.34 (d, J=7.8 Hz, 1H, Ar—H), 7.49 (t, J=8.3 Hz, 1H, Ar—H), 7.96 (d, J=6.9 Hz, 1H, Ar—H).; $^{13}$C-NMR (100 MHz, CDCl$_3$): δ49.07, 53.70, 54.52, 55.26, 59.43, 60.49, 116.01, 116.56, 119.67, 124.18, 125.2.6, 125.32, 129.05, 132.91, 147.35, 151.18, 152.04, 155.44.; Anal. Calcd for C$_{22}$H$_{25}$N$_5$O (375.47): C, 70.38; H, 6.71; N, 18.65. Found: C, 70.48; H, 6.67; N, 18.81.

EXAMPLE 14

3-{4-[1-(3-methoxyphenyl)piperazinyl]}methyl-5-methoxy-2,3-dihydroimidazo[1,2-c]quinazoline

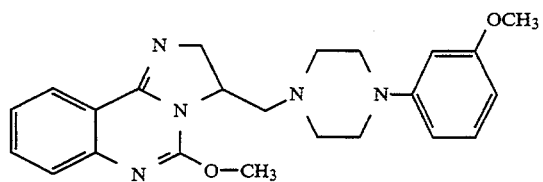

was obtained in 90% yield using a procedure similar to that of Example 12. An analytical sample was recrystallized from acetonitrile, mp 99°–100° C. ms: m/z 405 (M+), 270(M+−135), 243 (M+−162), 205 (M+−200, 100%).; $^1$H-NMR (400 MHz, DMSO-d$_6$): δ2.51–2.62 (m, 6H, 3CH$_2$), 3.09 (m, 4H, 2CH$_2$), 3.70 (s, 3H, CH$_3$), 3.95 (s, 3H, CH$_3$), 3.87–4.03 (m, 2H, CH2), 4.54 (m, 1H, CH), 6.35 (d, J=8.3 Hz, 1H, Ar—H), 6.43 (s, 1H, Ar—H), 6.49 (d, J=8.3 Hz, 1H, Ar—H), 7.09 (t, J=8.3 Hz, 1H, Ar—H), 7.19 (t, J=7.8 Hz, 1H, Ar—H), 7.27 (d, J=8.3 Hz, 1H, Ar—H), 7.51 (t, J=7.8 Hz, 1H, Ar—H), 7.82 (d, J=7.3 Hz, 1H, Ar—H).;−7.84 (m, 8H, Ar—H).; $^{13}$C-NMR (100 MHz, DMSO-d$_6$): δ48.13, 53.11, 54.53, 54.66, 54.79, 58.90, 59.98, 101.44, 104.02, 107.99, 116.42, 123.88, 124.94, 124.99, 129.53, 132.77, 147.05, 152.14, 152.28, 153.67, 160.15; Anal. Calcd for C$_{23}$H$_{27}$N$_5$O$_2$ (405.50): C, 68.13; H6.71; N, 17.27. Found: C, 67.77; H, 6.68; N, 17.67.

EXAMPLE 15

3-{4-[1-(4-methoxyphenyl)piperazinyl]}methyl-5-methoxy-2,3-dihydroimidazo[1,2-c]quinazoline

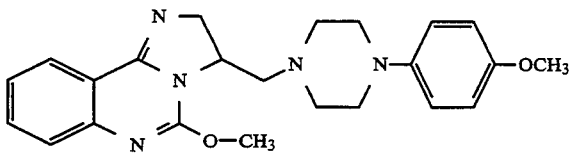

was obtained in 90.4% yield using a procedure similar to that of Example 12. An analytical sample was recrystallized from acetonitrile, mp 149°–150° C. ms: m/z 405 (M+); $^1$H-NMR (400 MHz, CDCl$_3$): δ2.21–2.76 (m, 6H, 3CH$_2$), 3.06–3.08 (m, 4H, 2CH$_2$), 3.76 (s, 3H, CH$_3$), 4.03 (s, 3H, CH$_3$), 4.05–4.19 (m, 2H, CH$_2$), 4.48–4.53 (m, 1H, CH), 6.86 (m, 4H, Ar—H), 7.18 (t, J=7.8 Hz, 1H, Ar—H), 7.34 (d, J=7.8 Hz, 1H, Ar—H), 7.49 (t, J=8.3 Hz, 1H, Ar—H), 7.96 (d, J=7.8 Hz, 1H, Ar—H).; $^{13}$C-NMR (100 MHz, CDCl$_3$): δ50.57, 53.83, 54.54, 55.29, 55.51, 59.39, 60.49, 114.38, 118.15, 124.20, 125.28, 125.35, 132.93, 145.60, 147.37, 152.05, 153.77, 155.47.; Anal. Calcd for C$_{23}$H$_{27}$N$_5$O$_2$ (405.50): C, 68.13; H, 6.71; N, 17.27. Found: C, 67.94; H, 6.61; N, 17.33.

EXAMPLE 16

3-{4-[1-(2-chlorophenyl)piperazinyl]}methyl-5-methoxy-2,3-dihydroimidazo[1,2-c]quinazoline

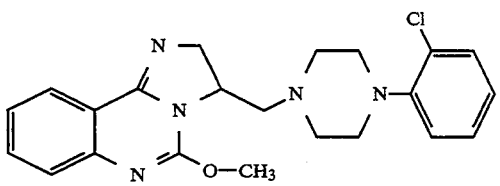

was obtained in 84% yield using a procedure similar to that of Example 12. An analytical sample was recrystallized from acetonitrile, mp 148°–149° C., $^1$H-NMR (400 MHz, DMSO-d$_6$): δ2.50–2.69 (m, 6H, 3CH$_2$), 2.96 (m, 4H, 2CH$_2$), 3.86–4.08 (m, 2H, CH$_2$), 3.96 (s, 3H, OCH$_3$), 4.57 (m, 1H, CH), 7.02 (t, J=7.8 Hz, 1H, Ar—H), 7.14 (d, J=7.8 Hz, 1H, Ar—H), 7.19 (t, J=7.4 Hz, 1H, Ar—H), 7.27 (d, J=8.3 Hz, 2H, Ar—H), 7.38 (d, J=7.8 Hz, 1H, Ar—H), 7.51 (t, J=7.4 Hz, 1H, Ar—H), 7.82 (d, J=7.8 Hz, 1H, Ar—H).; $^{13}$C-NMR (100 MHz, DMSO-d$_6$): δ50.80, 53.33, 54.55, 54.62, 58.87, 60.02, 116.40, 120.83, 123.81, 123.90, 124.96, 125.02, 127.58, 128.03, 130.26, 132.81, 147.05, 148.94, 152.15, 153.67.; Anal. Calcd for C$_{22}$H$_{24}$N$_5$OCl(409.92): C, 64.46; H, 5.90; N, 17.09. Found: C, 64.19; H, 5.87; N, 16.93.

EXAMPLE 17

3-(4-Phenyl-1-piperazinyl)-methyl-2,3-dihydroimidazo[1,2-c]quinazolin-5(6H)-one

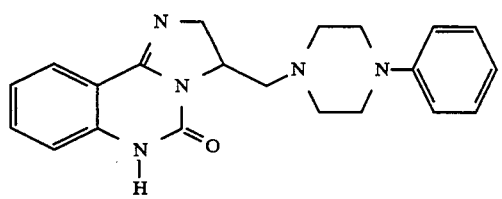

To a mixture of 3-{4-[1-(phenyl)piperazinyl]}methyl-5-methylthio-2,3-dihydroimidazo[1,2c]quinazoline (0.34 g, 0.87 mmol) in methanol (30 mL) was added sodium hydroxide (5 g, 0.1 mol). The mixture was refluxed using an oil bath for 6 hours. The mixture was then evaporated in vacuo to dryness. To the residue was added water 50 mL) and then was neutralized with acetic acid to pH 7. The resulting solid was collected by filtration to afford 0.29 g (93%) of 3-(4-phenyl-1-piperazinyl)-methyl-2,3-dihydro-imidazo[1,2-c]quinazolin-5(6H)-one. An analytical sample was recrystallized from ethanol, mp 252°–253° C.; $^1$H-NMR (400 MHz, DMSO-d$_6$): δ2.45–2.80 (m, 6H, 3 CH$_2$), 3.08 (m, 4H, 2CH$_2$), 3.86–4.06 (m, 2H, CH$_2$), 4.48 (m, 1H, CH), 6.73 (t, J=7.3 Hz, 1H, Ar—H), 6.89 (d, J=8.3 Hz, 2H, Ar—H), 7.06 (t, J=9.3 Hz, 2H, Ar—H), 7.18 (t, J=7.8 Hz, 2H, Ar—H), 7.47 (t, J=7.8 Hz, 1H, Ar—H), 7.78 (d, J=7.8 Hz, 1H, Ar—H), 10.55 (s, 1H, NH).; $^{13}$C-NMR (100 MHz, DMSO-d$_6$): δ48.10, 53.13, 53.71, 58.34, 59.03, 111.48, 114.92, 115.16, 118.54, 121.96, 125.47, 128.67, 132.79, 139.63, 148.00, 150.86, 152.41.; ms: m/z 361 (M+), 296 (M+ −65), 285 (M+ −76), 275 (M+ −86), 175 (M+ −185, 100%). Anal. Calcd for C$_{21}$H$_{23}$N$_5$O (361.45): C, 69.78; H, 6.41; N, 19.38. Found: C, 69.78; H, 6.43; N, 19.33.

EXAMPLE 18

3-{4-[1-(2-methoxyphenyl)piperazinyl]}methyl-2,3-dihydroimidazo[1,2-c]quinazolin-5(6H)-one

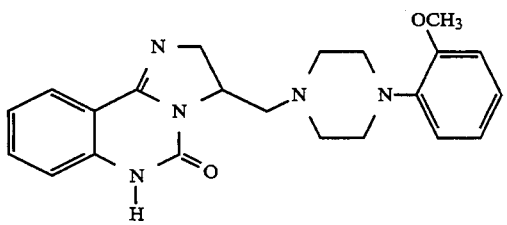

was obtained in 34% yield using a procedure similar to that of Example 17. An analytical sample was recrystallized from ethanol, mp 211°–212° C. IR (KBr): 1635, 1688, 2829, 2946, 3226 cm$^{-1}$; $^1$H-NMR (400 MHz, DMSO-d$_6$): δ2.45–2.85 (m, 6H, 3CH$_2$), 2.95 (m, 4H, 2CH$_2$), 3.77 (s, 3H, OCH$_3$), 3.87–4.08 (m, 2H, CH$_2$), 4.48 (m, 1H, CH), 6.86–6.94 (m, 4H, Ar—H), 7.09 (t, J=6.5 Hz, 2H, Ar—H), 7.48 (t, J=7.3 Hz, 1H, Ar—H), 7.80 (d, J=8.3 Hz, 1H, Ar—H), 10.50 (s, 1H, NH).; $^{13}$C-NMR (100 MHz, DMSO-d$_6$): δ50.05, 53.60, 53.67, 55.25, 58.47, 59.34, 111.56, 111.85, 115.10, 117.85, 120.81, 122.13, 122.31, 125.58, 132.99, 139.79, 141.18, 148.13, 151.94, 152.54.; ms:m/z 391 (M+), 376 (M+ −15), 205 (M+ −187, 100%). Anal. Calcd. for C$_{22}$H$_{25}$N$_5$O$_2$ (391.47): C, 67.50; H, 6.44; N, 17.89. Found: C, 67.40; H, 6.43; N, 17.83.

EXAMPLE 19

3-{4-[1-(3-methoxyphenyl)piperazinyl]}methyl-2,3-dihydroimidazo[1,2-c]-quinazolin-5(6H)-one

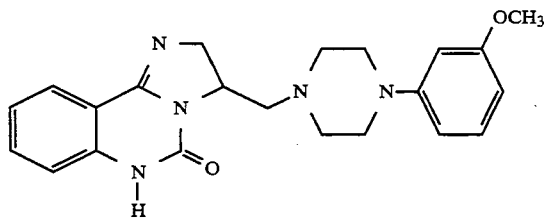

was obtained in 90% yield using a procedure similar to that of Example 17. An analytical sample was recrystallized from ethanol, mp 200°-201° C. ms: m/z 391 (M+), 376 (M+ −15), 205 (M+ −186, 100%).; $^1$H-NMR (400 MHz, CDCl$_3$): δ2.47-2.93 (m, 6H, 3CH$_2$), 3.09-4.12 (m, 4H, 2CH$_2$), 3.70 (s, 3H, OCH$_3$), 4.00-4.14 (m, 2H, CH$_2$), 4.50-4.52 (m, 1H, CH), 6.32-6.45 (m, 3H, Ar—H), 6.92 (d, J=8.3 Hz, 1H, Ar—H), 7.02-7.10 (m, 2H, Ar—H), 7.37 (t, J=7.4 Hz, 1H, Ar—H), 7.87 (d, J=7.8 Hz, 1H, Ar—H), 9.93 (s, 1H, NH).; $^{13}$C-NMR (100 MHz, CDCl$_3$): δ48.15, 53.23, 53.69, 54.81, 58.45, 59.16, 101.41, 104.06, 107.97, 111.56, 115.14, 122.11, 125.56, 129.53, 132.97, 139.83, 148.17, 152.34, 152.56, 160.15, 174.63. Anal. Calcd for C$_{22}$H$_{25}$N$_5$O$_2$ (391.47): C, 67.50; H, 6.44; N, 17.89. Found: C, 67.44; H, 6.34; N, 17.93.

EXAMPLE 20

3-{4-[1-(4-methoxyphenyl)piperazinyl]}methyl-2,3-dihydroimidazo[1,2-c]quinazolin-5(6H)-one

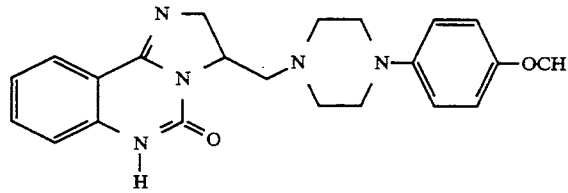

was obtained in 99% yield using a procedure similar to that of Example 17. An analytical sample was recrystallized from DMF, mp 250°-251° C. ms: m/z 391 (M+), 376 (M+ −15), 205 (M+ −171, 100%).; $^1$H-NMR (400 MHz, DMSO-d$_6$): δ2.50-2.82 (m, 6H, 3CH$_2$), 2.98 (br s, 4H, 2CH$_2$), 3.67 (s, 3H, OCH$_3$), 3.87-4.06 (m, 2H, CH$_2$), 4.47 (m, 1H, CH), 6.86 (d, J=8.7 Hz, 2H, Ar—H), 6.79 (d, J=8.7 Hz, 2H, Ar—H), 7.07 (d, J=6.4 Hz, 2H, Ar—H), 7.45 (t, J=7.3 Hz, 1H, Ar—H),, 7.78 (d, J=7.8 Hz, 1H, Ar—H), 10.85 (s, 1H, NH).; $^{13}$C-NMR (100 MHz, DMSO-d$_6$): δ49.50, 53.27, 53.75, 55.08, 58.32, 59.03, 111.48, 114.17, 115.01, 117.15, 121.92, 125.44, 132.79, 139.76, 145.30, 148.06, 152.47, 152.78. Anal. Calcd for C$_{22}$H$_{25}$N$_5$O$_2$ (391.47): C, 67.50; H, 6.44; N, 17.89. Found: C, 67.55; H, 6.38; N, 17.97.

EXAMPLE 21

3-{4-[1-(2-chlorophenyl)piperazinyl]}methyl-2,3-dihydroimidazo[1,2-c]quinazolin-5(6H)-one

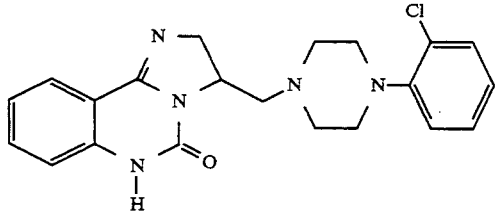

was obtained in 68% yield using a procedure similar to that of Example 17. An analytical sample was recrystallized from ethanol, mp 227°-228° C. ms: m/z 395 (M+); $^1$H-NMR (400 MHz, DMSO-d$_6$): δ2.45-2.86 (m, 6H, 3CH$_2$), 2.94 (m, 4H, 2CH$_2$), 3.85-4.06 (m, 2H, CH$_2$), 4.44-4.49 (m, 1H, CH), 6.98-7.12 (m, 4H, Ar—H), 7.25 (t, J=7.8 Hz, 1H, Ar—H), 7.34 (d, J=7.8 Hz, 1H, Ar—H), 7.45 (t, J=7.4 Hz, 1H, Ar—H), 7.77 (d, J=7.4 Hz, 1H, Ar—H), 10.51 (s, 1H, NH).; $^{13}$C-NMR (100 MHz, DMSO-d$_6$): δ50.82, 53.44, 53.67, 58.47, 59.23, 111.56, 115.05, 120.75, 122.13, 123.75, 125.58, 127.58, 127.98, 130.26, 132.97, 139.74, 148.09, 148.94, 152.50. Anal. Calcd for C$_{21}$H$_{22}$N$_5$OCl (395.89): C, 63.71; H, 5.60; N, 17.69. Found: C, 63.71; H, 5.66; N, 17.72.

EXAMPLE 22

3-{4-[1-(2-chlorophenyl)piperazinyl]}methyl-6-methyl-2,3-dihydroimidazo[1,2-c]quinazolin-5(6H)-one

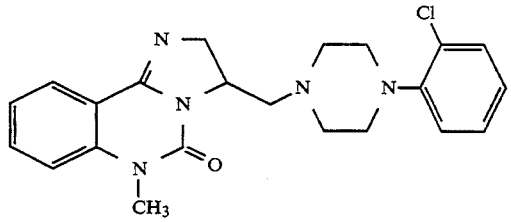

To a solution of 3-{4-[1-(2-chlorophenyl)piperazinyl]}methyl-2,3-dihydroimidazo[1,2-c]quinazolin-5(6H)-one (1.52 g, 3.8 mmol) in DMF (45 mL) was added 50% sodium hydride (0.4 g, 7.6 mmol). The solution was stirred at room temperature for 1 hour and then to the solution was added methyl iodide (0. 28 mL, 4.56 mmol). The resulting solution was stirred at room temperature and after 24 hours, the mixture was poured into ice water (200 mL) to get precipitates which was collected by filtration to give the title compound (1.4 g, 90%). An analytical sample was recrystallized from ethanol, m.p. 154°-155° C. $^1$H-NMR (400 MHz, DMSO-d$_6$): δ2.46-2.86 (m, 4H, 2CH$_2$), 2.70 (br, s, 1H, CH), 2.83-2.85 (m, 1H, CH), 2.96 (br s, 4H, 2CH$_2$), 3.36 (s, 3H, CH$_3$), 3.86-3.91 (m, 1H, CH), 4.01-4.08(m, 1H, CH), 4.52 (m, 1H, CH), 7.02 (t, J=7.4 Hz, 1H, Ar—H), 7.13 (d, J=8.3 Hz, 1H, Ar—H), 7.18 (t, J=7.8 Hz, 1H, Ar—H), 7.28 (m, 2H, Ar—H), 7.38 (d, J=7.8 Hz, 1H, Ar—H), 7.60 (t, J=7.8 Hz, 1H, Ar—H), 7.89 (d, J=7.8 Hz, 1H, Ar—H); $^{13}$C-NMR (100.40 MHz, DMSO-d$_6$): δ29.37, 50.80, 53.42, 54.79, 58.28, 59.20, 112.65, 114.63, 120.77, 122.40, 123.75, 125.73, 127.54, 128.00, 130.25, 133.30, 140.47, 148.09, 148.94, 151.57.; ms: m/z 409 (M+), 394 (M+ −15), 269 (M+ −140), 209 (M+ −200). Anal. Calcd for C$_{22}$H$_{24}$N$_5$OCl (409.92): C, 64.46; H, 5.90; N, 17.09. Found: C, 64.38; H, 5.90; N, 16.90.

EXAMPLE 23

3-{4-[1-(2-methoxyphenyl)piperazinyl]}methyl-6-methyl-2,3-dihydroimidazo[1,2-c]quinazolin-5(6H)-one

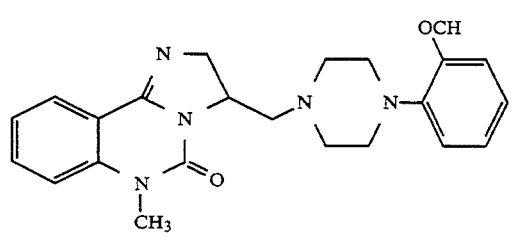

was obtained in 65% yield using a procedure similar to that of Example 22. Analytical sample was prepared by recrystallization from acetonitrile, mp 147°-148° C. ms: m/z 405 (M+); $^1$H-NMR (400 MHz, DMSO-d$_6$): δ2.43-2.50 (m, 4H, 2CH$_2$), 2.65 (m, 2H, CH$_2$), 2.80-2.94 (m, 4H, 2CH$_2$), 3.36 (s, 3H, CH$_3$), 3.76 (s, 3H, CH$_3$), 3.85-4.07 (m, 2H, CH$_2$), 4.50 (m, 1H, CH), 6.85-6.93 (m, 4H, Ar—H), 7.17 (t, J=7.8 Hz, 1H, Ar—H), 7.25 (d, J=8.3 Hz, 1H, Ar—H), 7.59 (t, J=7.4 Hz, 1H, Ar—H), 7.88 (d, J=7.8 Hz, 1H, Ar—H); $^{13}$C-NMR (100 MHz, DMSO-d$_6$): δ29.33, 50.02, 53.56, 54.79, 55.23, 58.30, 59.31, 11.85, 112.65, 114.57, 117.81, 120.77, 122.27, 125.71, 133.24, 140.43, 141.16, 148.06, 151.55, 151.92.; Anal. Calcd for C$_{23}$H$_{27}$N$_5$O$_2$ (405.50): C, 68.13; H, 6.71; N, 17.27. Found:, C, 68.17; H, 6.63; N, 17.23.

EXAMPLE 24

3-{4-[1-(3-methoxyphenyl)piperazinyl]}methyl-6-methyl-2,3-dihydroimidazo[1,2-c]quinazolin-5(6H)-one

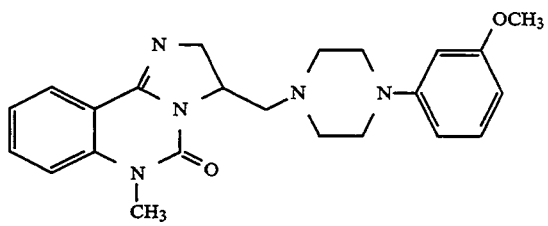

was obtained in 84% yield using a procedure similar to that of Example 22. Analytical sample was prepared by recrystallization from acetonitrile, mp 139°-140° C.; ms: m/z 405 (M+); $^1$H-NMR (400 MHz, CDCl$_3$): δ2.50-2.98 (m, 6H, 3CH$_2$), 3.16-3.17 (m, 4H, 2CH$_2$), 3.45 (s, 3H, OCH$_3$), 3.77 (s, 3H, CH$_3$), 4.05-4.18 (m, 2H, CH$_2$), 4.59 (m, 1H, CH), 6.40 (d, J=8.3 Hz, 1H, Ar—H), 6.44 (s, 1H, Ar—H), 6.51 (d, J=8.3 Hz, 1H, Ar—H), 7.06 (d, J=8.3 Hz, 1H, Ar—H), 7.13-7.26 (m, 3H, Ar—H), 7.54 (t, J=8.3 Hz, 1H, Ar—H), 8.03 (d, J=7.8 Hz, 1H, Ar—H); $^{13}$C-NMR (100 MHz, CDCl$_3$): δ29.91, 49.28, 53.99, 55.40, 55.64, 59.28, 60.05, 102.64, 104.65, 109.04, 113.47, 114.20, 123.07, 126.87, 129.98, 133.62, 140.99, 149.09, 152.93, 153.10, 160.80. Anal. Calcd for C$_{23}$H$_{27}$N$_5$O$_2$ (405.50): C, 68.13; H, 6.71; N, 17.27. Found:, C, 68.18; H, 6.65; N, 17.20.

EXAMPLE 25

6,7-Dimethoxyquinazolin-2,4(1H, 3H)-dithione

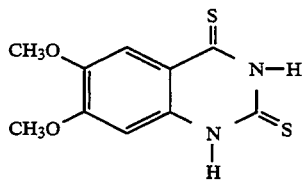

A mixture of 4,5-dimethylanthranilonitrile (10 g, 56.2 mmol) and carbon disulfide (30 ml, 0.4 mmol) in pyridine (90 mL) was refluxed using an oil bath. After 8 hours, the mixture was cooled to room temperature and to this solution was added ethanol (250 mL). The yellowish solid was then collected and washed with ether (10 mL) to give 13.28 g (93%) of 6,7-dimethoxyquinazolin-2,4(1H, 3H)-dithione. $^1$H-NMR (100 MHz, DMSO-d$_6$): δ3.83 (s, 3H, CH$_3$), 3.86 (s, 3H, CH$_3$), 6.86 (s, 1H, Ar—H), 7.68 (s, 1H, Ar—H), 12.96 (s, 1H, NH, D$_2$O exchangeable), 13.47 (s, 1H, NH, D$_2$O exchangeable); ms: m/z 254 (M+), 238 (M+—16), 221 (M+—33), 196 (M+—58), 180 (M+—74).

EXAMPLE 26

2,4-dimethylthio-6,7-dimethoxyquinazoline

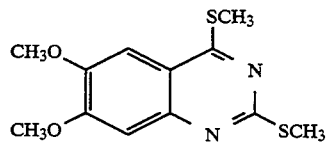

was obtained in 95% yield using a procedure similar to that of Example 2.; $^1$H-NMR (100 MHz, DMSO-d$_6$): δ2.59 (s, 3H, CH$_3$), 2.65 (s, 3H, CH$_3$); 3.91 (s, 3H, CH$_3$), 3.94 (s, 3H, CH$_3$), 7.10 (s, 1H, Ar—H), 7.15 (s, 1H, Ar—H).; ms: m/z 282 (M+), 268 (M+—14), 249 (M+—33), 235 (M+—47), 221 (M+—61), 204 (M+—78), 189 (M+—93), 177 (M+—105).

EXAMPLE 27

4-Allylamino-6,7-dimethoxy-2-methylthioquinazoline

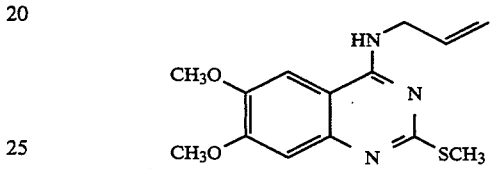

was obtained in 32% yield using a procedure similar to that of Example 3. mp 122°-124° C.

EXAMPLE 28

3-Bromomethyl-5-methylthio-8,9-dimethoxy-2,3-dihydroimidazo[1,2-c]quinazoline

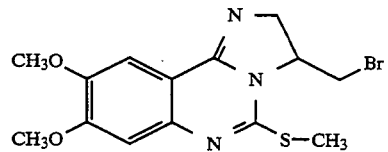

was obtained in 75% yield using a procedure similar to that of Example 4. An analytical sample was recrystallized from acetonitrile, mp 225° C. ms: m/z 371 (M++1), 369 (M+—1), 356 (M+—14), 354 (M+—80).

EXAMPLE 29

3-[4-(1-phenyl)piperazinyl]methyl-5-methylthio-8,9-dimethoxy-2,3-dihydroimidazo-[1,2-c]quinazoline

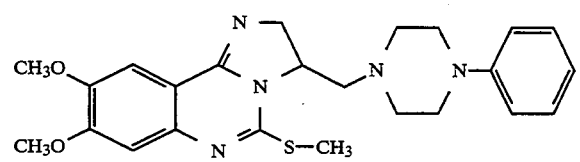

A mixture of 3-bromomethyl-5-methylthio-8,9-dimethyoxy-2,3-dihydroimidazo[1,2-c]quinazoline (0.36 g, 0.97 mmol), 1-phenylpiperazine (0.3 mL, 1.85 mmol) and sodium hydrogen carbonate (0.1 g, 1.2 mmol) in acetonitrile (40 mL) was refluxed using an oil bath. After 18 hours, the mixture was cooled to room temperature and the solid was then collected by filtration and washed with water (20 mL) to give 0.32 g (53%) of 3-[4-(1-phenyl)piperazinyl]methyl-5-methylthio-8,9-dimethoxy-2,3-dihydroimidazo-[1,2-c]-quinazoline. An analytical sample was recrystallized from acetonitrile, mp 207°–209° C. $^1$H-NMR (300 MHz, DMSO-d$_6$): δ2.40–2.52 (m, 2H, CH$_2$), 2.55 (s, 3H, SCH$_3$), 2.70–2.73 (m, 4H, 2CH$_2$), 3.12 (m, 4H, 2CH$_2$), 3.79 (s, 3H, CH$_3$), 3.84 (s, 3H, CH$_3$), 3.91–4.05 (m, 2H, CH$_2$), 4.53 (m, 1H, CH), 6.76 (t, 1H, J=7.1 Hz, Ar—H), 6.86 (s, 1H, Ar—H), 6.91 (d, 2H, J=8.2 Hz, Ar—H), 7.17–7.22 (m, 3H, Ar—H).; $^{13}$C-NMR (75 MHz, DMSO-d$_6$):δ13.08, 48.12, 53.10, 55.56, 55.95, 58.49, 59.28, 105.07, 107.38, 108.94, 115.34, 118.77, 128.85, 141.54, 147.17, 150.91, 152.13, 152.36, 153.09.; ms: m/z 451 (M+), 404 (M+−47), 320 (M+−131), 277 (M+−174). Anal. Calcd for C$_{24}$H$_{29}$N$_5$SO$_2$ (451.59): C, 63.83; H, 6.47; N, 15.51. Found: C, 63.75; H, 6.48; N, 15.57.

What is claimed is:

1. An imidazo[1,2-c]quinazoline compound having the formula

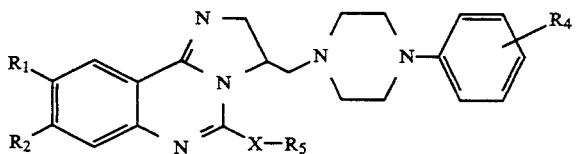

which comprises racemic mixture of optically active compounds or optically pure R and S stereoisomers, wherein:

X is S or O, when X is S, the formula represents I; and when X is O, the formula represents II:

R$_1$ is halogen, hydrogen, C$_1$-C$_6$ alkyl, trifluoromethyl, or C$_1$-C$_6$ alkoxy;

R$_2$ is halogen, hydrogen, C$_1$-C$_6$ alkyl, trifluoromethyl, or C$_1$-C$_6$ alkoxy;

R$_4$ is halogen, hydrogen, methoxy, trifluoromethyl, C$_1$-C$_4$ alkyl, nitro, acetyl, cyano or hydroxy group;

R$_5$ is C$_1$-C$_4$ alkyl group;

or pharmaceutically acceptable salts thereof.

2. An imidazo[1,2-c]quinazoline compound or a pharmaceutically acceptable salt thereof, as claimed in claim 1, which is selected from a class of compounds consisting of:

3-[4-(1-Phenyl)piperazinyl]methyl-5-methylthio-2,3-dihydroimidazo[1,2-c]quinazoline;

3-{4-[1-(2-methoxyphenyl)piperazinyl]}methyl-5-methylthio-2,3-dihydroimidazo[1,2-c]quinazoline;

3-{4-[1-(2-chlorophenyl)piperazinyl]}methyl-5-methylthio-2,3-dihydroimidazo[1,2-c]quinazoline;

3-{4-[1-(2-Methoxyphenyl)piperazinyl]}methyl-5-methoxy-2,3-dihydroimidazo[1,2-c]quinazoline;

3-[4-(1-phenyl)piperazinyl]methyl-5-methylthio-8,9-dimethoxy-2,3-dihydroimidazo[1,2-c]quinazoline;

3-{4-[1-(phenyl)piperazinyl]}methyl-5-methoxy-2,3-dihydroimidazo[1,2-c]quinazoline;

3-{4-[1-(2-chlorophenyl)piperazinyl[}methyl-5-methoxy-2,3-dihydroimidazo[1,2-c]quinazoline.

3. A pharmaceutical composition for the treatment of hypertension or dysuria, which comprises a therapeutically effective amount of an imidazo[1,2-c]quinazoline compound of the formula I as set forth in claim 1 or a pharmaceutically acceptable salt thereof, as an active ingredient, in admixture with a pharmaceutically acceptable carrier or diluent for the active ingredient.

4. A method for tile treatment of hypertension compromising administering a therapeutically effective amount of an imidazo[1,2-c]quinazoline compound of the formula I as set forth in claim 1 to a subject suffering from high blood pressure.

5. A pharmaceutical composition for the treatment of hypertension or dysuria, which comprises a therapeutically effective amount of an imidazo[1,2c]quinazoline compound of the formula II as set forth in claim 1 or a pharmaceutically acceptable salt thereof, as an active ingredient, in admixture with a pharmaceutically acceptable carrier or diluent for the active ingredient.

6. A method for the treatment of hypertension compromising administering a therapeutically effective amount of an imidazo[1,2-c]quinazoline compound of the formula II as set forth in claim 1 to a subject suffering from high blood pressure.

7. A method for the treatment of dysuria compromising administering a therapeutically effective amount of an imidazo[1,2-c]quinazoline compound of the formula I as set forth in claim 1 to a subject suffering from prostatauxe.

8. A method for the treatment of dysuria compromising administering a therapeutically effective amount of an imidazo[1,2-c]quinazoline compound of the formula II as set forth in claim 1 to a subject suffering from prostatauxe.

* * * * *

UNITED STATES PATENT AND TRADEMARK OFFICE
CERTIFICATE OF CORRECTION

PATENT NO. : 5,340,814
DATED : August 23, 1994
INVENTOR(S) : Ji-Wang Chern, et al.

It is certified that error appears in the above-indentified patent and that said Letters Patent is hereby corrected as shown below:

Col. 1, line 41, following "5,158,953", insert -- ) --.

Col. 2, line 26, delete "II:" and insert -- II; --.

Col. 2, line 67, delete "hydrates" and insert -- hydrate --.

Col. 5, line 16, delete "cesium carbonate" and insert -- cesiumcarbonate --.

Col. 5, line 46, delete "6-20" and insert -- 16-20/min--.

Col. 10, line 3, delete "(m3H," and insert -- (m, 3H --.

Col. 10, line 5, delete "Ar-, H" and insert -- Ar-H --.

Col. 14, line 27, delete "125.2.6" and insert -- 125.26 --.

Col. 14, line 63, delete "H6.71" and insert -- H,6.71 --.

Col. 16, line 3, delete "water 50 mL)" and insert -- water (50 mL) --.

Col. 17, line 23, in the compound far right, delete "OCH" insert --$OCH_3$--.

Col. 18, line 51, in the compound far right, delete "OCH" insert --$OCH_3$--.

UNITED STATES PATENT AND TRADEMARK OFFICE
CERTIFICATE OF CORRECTION

PATENT NO. : 5,340,814
DATED : August 23, 1994
INVENTOR(S) : Ji-Wang Chern, et al.

It is certified that error appears in the above-indentified patent and that said Letters Patent is hereby corrected as shown below:

Col. 22, line 11, delete "piperazinyl[} and insert -- piperazinyl]} --.

Col. 22, line 20, delete "tile" and insert -- the --.

Col. 22, line 27, delete "[1,2c]" and insert -- [1,2-c] --.

Signed and Sealed this

Twenty-second Day of August, 1995

Attest:

BRUCE LEHMAN

*Attesting Officer*     *Commissioner of Patents and Trademarks*